United States Patent [19]
Sullivan

[11] Patent Number: 4,856,116
[45] Date of Patent: Aug. 15, 1989

[54] SWEATBANDS

[76] Inventor: Lloyd S. Sullivan, c/o Osoli, Inc., 1516 Second Ave., #300, Seattle, Wash. 98101

[21] Appl. No.: 216,078

[22] Filed: Jul. 7, 1988

[51] Int. Cl.$^4$ .......................... A42C 5/02; A42B 1/18
[52] U.S. Cl. ............................................. 2/181; 2/12; 2/DIG. 11
[58] Field of Search ........................ 2/10, 12, 170, 171, 2/171.5, 177, 184, 181, 191, 196, 197, 209.1, 425, 452, DIG. 11, 179

[56] References Cited

U.S. PATENT DOCUMENTS

| | | | |
|---|---|---|---|
| 1,434,854 | 11/1922 | Stall | 2/181 X |
| 1,484,042 | 2/1924 | Smilie | 2/171 X |
| 1,974,258 | 9/1934 | Cavanagh | |
| 2,090,317 | 6/1935 | Underhill | |
| 2,127,926 | 3/1935 | Mason | |
| 3,184,758 | 11/1962 | Hirsch | |
| 3,280,406 | 11/1964 | Immel | |
| 3,466,664 | 6/1967 | Militello | |
| 4,130,902 | 12/1978 | Mackenroth, III et al. | 2/7 |
| 4,393,519 | 7/1983 | Nicastro | 2/DIG. 11 X |
| 4,578,822 | 4/1986 | Schmidthaler | 2/12 |
| 4,606,077 | 8/1986 | Phillips | 2/12 |
| 4,621,378 | 11/1986 | Hatchman | 2/12 |
| 4,630,317 | 12/1986 | Brown et al. | 2/12 |
| 4,698,852 | 10/1987 | Romero | |

FOREIGN PATENT DOCUMENTS

| | | | |
|---|---|---|---|
| 2039725 | 8/1980 | Canada | 2/12 |
| 2390116 | 12/1978 | France | |

Primary Examiner—Werner H. Schroeder
Assistant Examiner—Sara M. Current
Attorney, Agent, or Firm—Hughes & Multer

[57] ABSTRACT

A sweatband which has a first component for absorbing copious quantities of perspiration from a user's skin and a second component for holding the first component against that part of the user's body from which perspiration is to be adsorbed. The moisture absorbing component has a core of moisture absorbent material covered with a soft, pliable material which will be comfortable to the user and will efficiently promote the absorption of moisture from the user's skin and the transfer of that moisture to the absorbent core. The second component of the sweatband includes an elongated, elastically extensible member with the ends thereof fixed to opposite ends of the first sweatband component. A visor may be attached to the sweatband to provide an article of apparel which is capable of absorbing perspiration from a user's forehead and of simultaneously shielding the user's eyes and face from the elements.

17 Claims, 3 Drawing Sheets

SWEATBANDS

TECHNICAL FIELD OF THE INVENTION

In one aspect, the present invention relates to novel, improved sweatbands.

And, in a second aspect, the present invention relates to novel, improved articles of apparel which combine a sweatband with a visor and are therefore capable of absorbing perspiration from the user's forehead and of shielding his or her eyes from the rays of the sun, rain, mist, etc.

BACKGROUND OF THE INVENTION

Conventionally, sweatbands are manufactured from a fabric such as terrycloth which has an open weave and is therefore moisture absorbent. Often, a fabric of this character with elastisized threads woven through it is employed to assist in retaining the sweatband in place when it is worn.

Sweatbands of the character just described are deficient in that the fabrics of which they are manufactured do not have the moisture absorbing capability desirable for a sweatband. Therefore, if the sweatband is fabricated in a practical width and thickness, it may rapidly be saturated by perspiration and become non-functional. On the other hand, if a sweatband were fabricated with sufficient material to have an adequate perspiration absorbing capability (perhaps comparable to that obtained by winding a towel turban fashion around the user's head), the sweatband would be so bulky and cumbersome as to be uncomfortable, if not entirely unusable.

SUMMARY OF THE INVENTION

I have now invented, and disclosed herein, certain new and novel sweatbands which differ markedly from those of conventional construction in that, even though relatively narrow and thin, they have sufficient moisture absorbing capacity to keep them from becoming saturated, even if the user is engaged in aerobic activities and perspiring freely. At the same time, these novel sweatbands are: of a simple construction and can accordingly be produced easily at a modest cost; light and comfortable to wear; and aesthetically pleasing.

Briefly, my novel sweatbands—normally designed to absorb sweat from the forehead or wrist of the user—have a first, perspiration absorbing component and a second component for holding the moisture absorbing component against the body surface from which the perspiration is to be absorbed.

The moisture absorbing component has an elongated core fabricated from a material with a high coefficient of absorption, typically a predominantly open cell, synthetic polymer. The rear, inner, or body surface-engaging side of the core is covered or faced with a soft, pliable material which the user will find comfortable. I furthermore employ a material which is capable of absorbing copious amounts of perspiration from the user's body and of transferring moisture beyond its capacity to retain to the core of the moisture absorbing sweatband component.

The outer or front side of the moisture absorbing core; i.e., that surface removed from the body of the user, is covered or faced with a natural, synthetic, or blended fabric to protect the core and to present a more pleasing appearance. This cover and the inner, moisture absorbing cover combine to surround the moisture absorbent core.

The outer cover is made from a fabric having a relatively porous woven or nonwoven structure. This promotes the evaporation of moisture from the absorbent core into the ambient surroundings, further ensuring that the absorbent core will not become saturated and non-functional like conventional terrycloth sweatbands. Almost a limitless variety of conventional and designer fabrics meet this specification, allowing my novel sweatbands to be manufactured in a correspondingly unlimited variety of colors and designs.

The second or retainer component of my novel sweatbands includes an elongated, elastically extensible member, and the opposite ends of this member are joined to one and the other ends of the moisture absorbing sweatband component. Thus, the retainer component can be stretched for ease in donning the sweatband; and it will then relax, holding the sweatband securely but comfortably in place with its inner, moisture absorbing covering against the body surface from which perspiration is to be absorbed. For aesthetic purposes and for protection, the elastically extensible member of the retainer component is preferably covered with an appropriate, eye pleasing fabric.

Sweatbands are often employed in circumstances in which the eyes and face of the user could be beneficially shielded from the elements (typically the sun's rays, but also rain and other moisture). I have also invented, and disclosed herein, a novel article of apparel which meets this goal and is, at the same time, capable of efficiently absorbing perspiration (and perhaps other moisture) from the forehead, wrist, or other anatomical portion of the user's body. Again speaking briefly, this novel article of apparel is an assembly of a sweatband as described above and a more-or-less conventional visor.

The visor may be fabricated from a wide variety of transparent, translucent, and/or opaque polymers or from other materials such as cardboard; or it may have a fabric over frame construction, for example. The particular materials that are employed will typically depend upon such factors as cost, ease of manufacture, the appearance which the visor is to have and the use to which it is to be put. For example, cardboard would perhaps not be suitable if the visor were to be used to shield the wearer from rain or other moisture but might be acceptable as a sunshield.

Integral, resiliently displaceable tabs may be provided to secure the crown and sidepieces of the visor to the sweatband. This scheme allows the visor to be removed so that the sweatband can be machine washed (In a typical application of my invention, all of the sweatband components will be machine washable, which is a decided practical advantage of the invention).

THE PRIOR ART

A headband which, at first blush, appears to resemble those we have invented is disclosed in U.S. Pat. No. 4,698,852 issued 13 Oct. 1987 to Romero. However, the Romera headband is designed to perform an entirely different function; and it is constructed in a manner that would make it unusable as a sweatband.

In particular, and as discussed above, my novel sweatbands have a moisture absorbing component with a highly absorbent central layer or core. A core of this character would be completely inappropriate for a Romero-type headguard which is designed to protect a soccer player from injury when he heads a ball. If the type of core critical to the successful performance of my novel sweatbands were employed in a Romero-type artifact, the latter would become impractical because, if a ball were headed after the artifact had been worn for any length of time, the impacting ball would compress the core and send cascades of perspiration into the player's eyes.

Also, the Romero headband has a suede outer layer which: "frictionally grips and halts the rotation of a soccer ball . . . " If the Romero headguard were fabricated with a moisture absorbent core like I employ, this outer, suede layer would soon become saturated and slick and therefore incapable of functioning as intended.

Quite aside from the foregoing, the Romero construction is quite different from mine, and impractical as far as a sweatband is concerned, because the inner, central, and outer layers of his headguard are adhesively bonded together. This construction is impractical for a multicomponent sweatband as the adhesive would unacceptably impede the migration of perspiration from the user's body through the inner covering to the core of the band and the evaporation of moisture from that core through the outer covering. As discussed above, both of these moisture transfer mechanisms are important in my novel sweatbands. Transfer of moisture from the inner covering to the core is necessary to keep the absorbent inner cover from becoming saturated. And migration of accumulated moisture from the core through the outer covering to the ambient surroundings is relied upon to keep the core from becoming saturated.

OBJECTS OF THE INVENTION

From the foregoing, it will be apparent to the reader that one primary and important object of the invention resides in the provision of novel, improved sweatbands.

Related and also important but more specific objects of the invention reside in the provision of sweatbands as characterized in the preceding object:

- which are capable of absorbing many times the amount of perspiration that can be absorbed by a conventional sweatband such as one fabricated from terry cloth;
- which are machine washable;
- which have a fabric outer covering and can accordingly readily be supplied in a variety of aesthetically appealing designs;
- which, in conjunction with the preceding object, are significantly more attractive than heretofore available sweatbands;
- which are light and otherwise comforatable to wear;
- which can easily be combined with a transparent, translucent, or opaque visor to provide an article of apparel that is capable of both absorbing perspiration from a user's forehead and shielding his or her eyes from the rays of the sun and other elements;
- which when combined with a visor as described in the preceding object, provide an article of apparel that can be provided in a variety of aesthetically pleasing styles, yet retains such attributes as the ability to absorb copious amounts of perspiration, lightness of weight, and comfortable wearability; and
- which can be manufactured at a relatively modes cost, whether or not the sweatband is combined with a visor.

Other important objects and features and additional advantages of the invention will be apparent to the reader from the foregoing and the appended claims and as the ensuing detailed description and discussion proceeds in conjunction with the accompanying drawing.

DETAILED DESCRIPTION OF THE INVENTION

Figure 1:
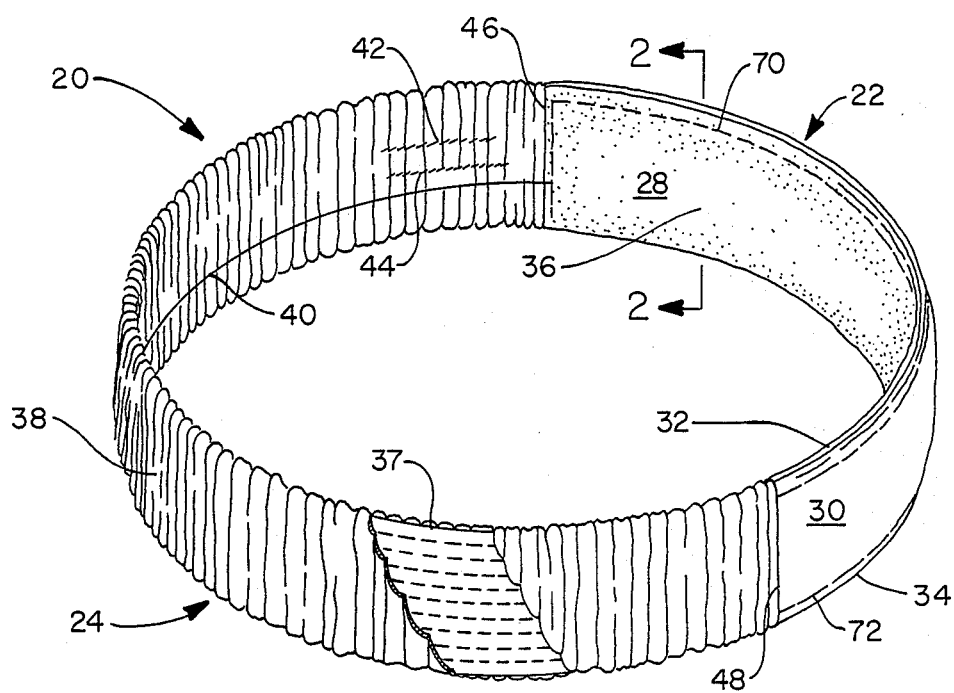
FIG. 1 is a pictorial view of a sweatband constructed in accord with and embodying the principles of the present invention.
Figure 2:
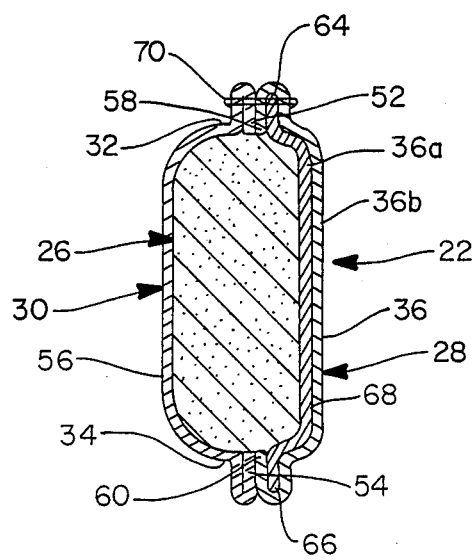
FIG. 2 is a section through the sweatband of FIG. 1, taken substantially along line 2—2 of the latter figure.

Referring now to the drawing, FIGS. 1 and 2 depict a sweatband 20 constructed in accord with, and embodying, the principles of the present invention. Sweatband 20 will typically be dimensioned to fit the forehead of the user or his or her wrist.

Sweatband 20 has a first component 22 for absorbing perspiration from a wanted part of the user's anatomy and a second component 24 for securing sweatband 20 in place.

As best shown in FIG. 2, the perspiration absorbing component 22 of sweatband 20 has a central member of core 26, a cover 28 on the inner side of core 26, and a an outer cover 30 which is joined to inner cover 28 at the top and bottom edges 32 and 34 of sweatband 20. The inner and outer covers 28 and 30 completely surround the core 26 of the sweatband.

The core 26 of perspiration absorbing sweatband component 22 acts as a reservoir for the perspiration absorbed from the user. I consequently prefer to fabricate this component from a porous, synthetic polymer having predominantly open cells—such as a hydrophilated polyester—so that core 26 will have a high ratio of absorptivity to volume. Other materials such as natural sponge may alternatively be employed but they will typically be less efficient and/or more expensive.

The illustrated core 26 has an elongated, generally rectangular cross-sectional configuration. This configuration provides a component 22 with an inner edge 36 which can lie flat against the user's forehead, wrist, or other body part. The configuration in question also promotes the transfer of perspiration from the user's body to core 26 inasmuch as it provides a surface with a large area apposite the user's body.

It is the function of the inner covering 28 of component 22 to absorb perspiration from the user's body and, as it becomes saturated, to transfer perspiration beyond its capacity to absorb to the core 26 of perspiration absorbing component 22. It is also necessary that inner covering 28 to be soft and flexible so that sweatband 20 will be comfortable to wear.

The preferred material for inner covering 28 is the cod oil tanned leather known as chamois. This material, employed in two layers 36a and 36b in sweatband component 24 (see FIG. 1), has all of the requisite properties. It is soft and pliable, has a high coefficient of absorptivity, and has a cellular structure which promotes the transfer of the perspiration it absorbs to the core 26 of sweatband component 22.

The outer cover or covering 30 of perspiration absorbing sweatband component 22 is provided for aesthetic purposes and to protect the core 26 of the perspiration absorbing sweatband component. Perhaps the most important criterion that must be observed in selecting a fabric (or other material) for outer covering 30 is that it must allow absorbed perspiration to freely escape into the ambient surroundings from the core 26 of perspiration absorbing component 22 so that the sweat absorbing component will not become saturated and thereafter fail to function. This requires that the material have a weave or other structure with high porosity. Even taking this criterion into account, there is a wide variety of materials, including designer fabrics, from which the outer covering can be made. As a consequence, the appearance of sweatband 20 can be varied in an almost endless fashion; and the sweatband can be produced in styles which will appeal to widely differing groups of users.

Referring still to FIGS. 1 and 2, the second sweatband components 24—employed to hold sweatband 20 in place with its inner covering 28 against that part of the user's body from which perspiration is to be absorbed—includes an elongated, elastically extensible member 37 surrounded by a cover 38, again for the purposes of protection and aesthetic appeal.

Cover 38 and the outer cover 30 of perspiration absorbing sweatband component 22 may be supplied as a single panel, or they may be independent components. In either case, the overlapping edges of the material covering elastically extensible member 37 (one shown in FIG. 1 and identified by reference character 40) will typically be stitched or otherwise joined together on the inner side of sweatband 20. Two rows of stitching are typically employed. They are illustrated diagrammatically in FIG. 1 only and are identified by reference characters 42 and 44.

Sweatband 20 has a circular configuration obtained by joining one end of elastically extensible member 37 to the apposite end 46 of perspiration absorbing sweatband component 22 and the other end of the elastically extensible member to the opposite end 48 of the perspiration absorbing component. The sweatband is employed in an obvious manner; i.e., donned by stretching extensible member 37 which, when then relaxed, holds sweatband 20 securely in place. In this respect, and is apparent from FIG. 1, the covering 38 around the extensible member 37 of sweatband retaining component 24 is much longer than the relaxed extensible member 37. This, which gives component 24 a corrugated appearance when the extensible member is relaxed, accommodates the increase in length of extensible member 37 when sweatband 20 is donned.

The preferred method of assembling sweatband component 22 is shown in FIG. 2. In particular, the upper and lower edges 52 and 54 of the outer covering 30 of perspiration absorbing, sweatband component 22 are folded against the main body portion 56 of that component for purposes of reinforcement. In a similar, but somewhat different, manner the upper and lower edge portions 58 and 60 of the inner, moisture absorbent covering outer layer 36b are trained around the upper and lower edges 64 and 66 of the inner layer 36a of cover 28 and lie parallel to the main body portion 68 of the layer 36a of the inner cover 28 of perspiration absorbing component 22. The outer and inner coverings 30 and 28 are then stitched together at the upper edge 32 of component 22 by thread 70 and at the lower edge 34 of the component by thread 72.

Alternatively, the inner and outer coverings 28 and 30 of the perspiration absorbing component 22 could be bonded to the core 26 of that component with an appropriate adhesive; and the ends of the elastically extensible member 37 of sweatband retaining component 24 could similarly be bonded to inner covering 28. However, as suggested above in the PRIOR ART section of this specification, I consider this assembly technique decidedly inferior as it would inhibit the transfer of perspiration from the absorbent inner covering 28 to the central reservoir or core 26 of the perspiration absorbing component. An adhesive layer would similarly and undesirably inhibit the desired evaporation of moisture absorbed by core 26 through outer covering 30 to the ambient surroundings.

I pointed out above that a more-or-less conventional visor may be assembled to a sweatband of the character just described to provide an article of apparel which has two, often desirably associated capabilities in that it can absorb perspiration from a user's forehead and, at the same time, shield his or her eyes and the upper portion of the user's face from the elements; viz., the sun's rays and rain, mist, and other moisture. An article of apparel of the character just described and having the just-enumerated capabilities is illustrated in FIG. 3 and identified by reference character 76.

Turning now to the Figures just mentioned, the sweatband of article 76 may be identified to the sweatband described above and illustrated in FIGS. 1 and 2. That sweatband has, therefore, also been identified in FIGS. 3 and 4 by reference character 20.

The visor 78 assembled to sweatband 20 to provide article of apparel 76 has a bill 80, a crown 82, and rearwardly extending sidepieces 84 and 86 at opposite sides of the visor's bill 80 and crown 82. Visor 78 may, depending upon the particular use contemplated for article of manufacture 76, be fabricated from an appropriate transparent, translucent, or opaque plastic, cardboard, etc. or a combination of materials. Alternative methods of fabricating the visor may also be employed. For example, a fabric over frame construction may be used. Thus, the visor can be made available in a wide variety of materials and configurations. Again, therefore, an article which a targeted group of users will find aesthetically appealing can easily be supplied.

Figure 3:
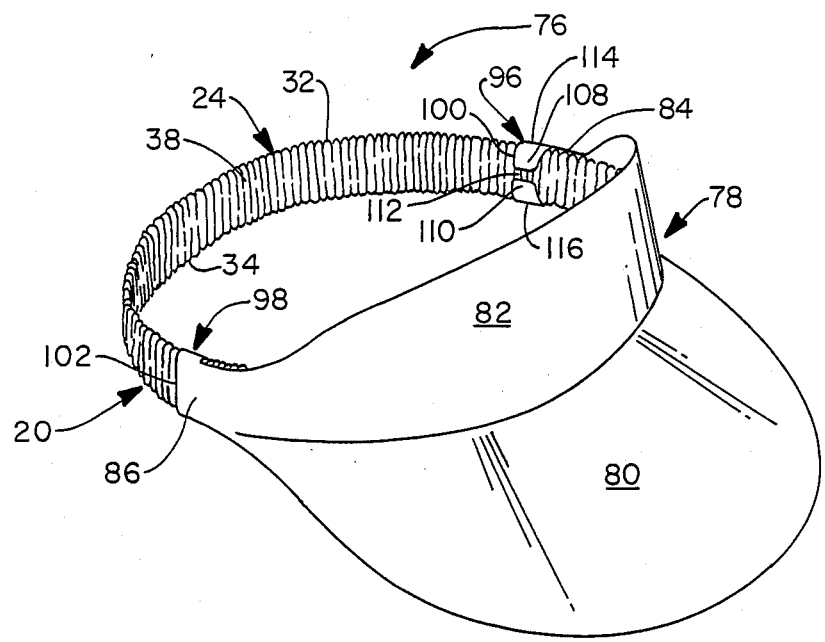
FIG. 3 is a pictorial view, looking from the front toward the back, of an article of apparel which is constructed in accord with and embodies the principles of my invention and consists of a visor assembled in fixed relationship to a sweatband of the character illustrated in FIG. 1.
Figure 4:
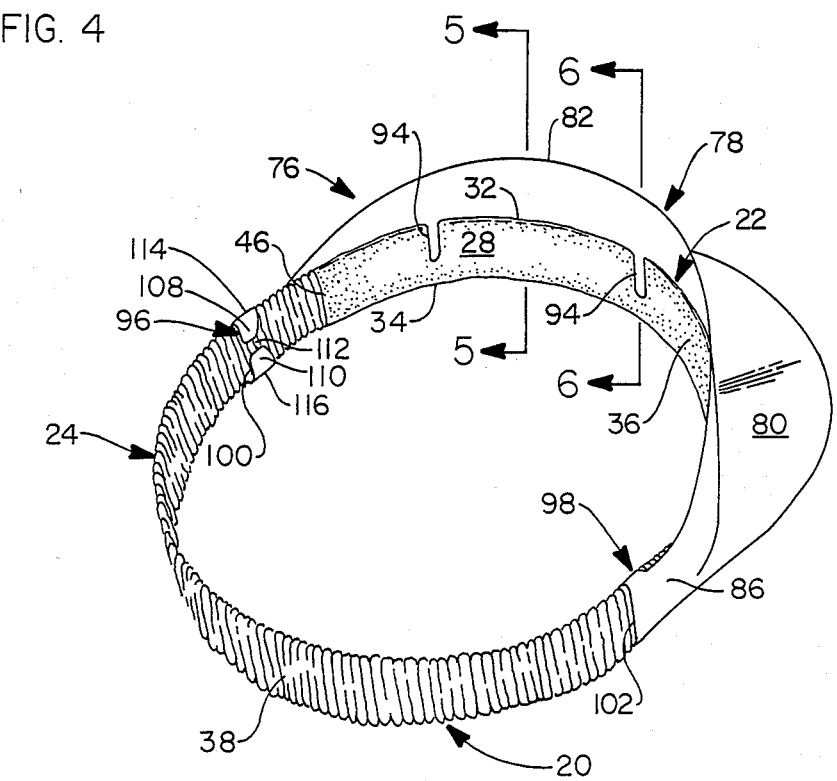
FIG. 4 is a view similar to FIG. 3 looking down on, and from the back toward the front of, the article shown in FIG. 3.
Figure 5:
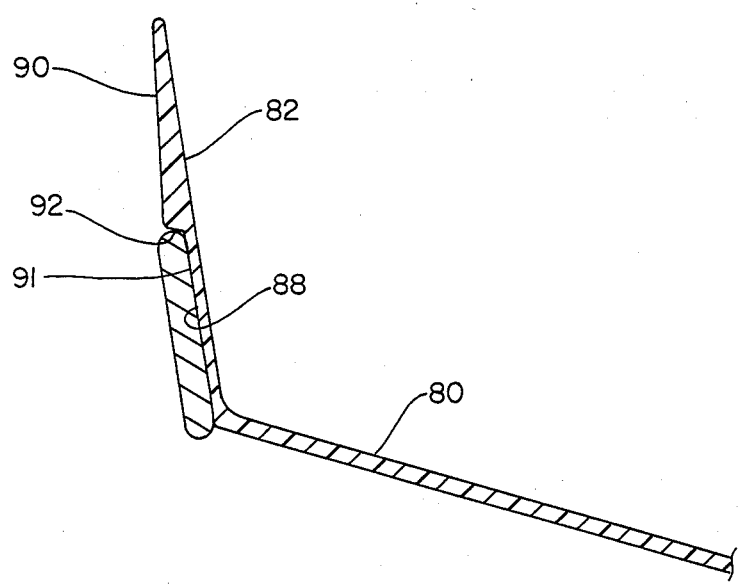
FIGS. 5 and 6 are sections through the article of apparel depicted in FIG. 4, the sweatband of the article being depicted in simplified form and the sections being taken substantially along lines 5—5 and 6—6 of FIG. 4.
Figure 6:
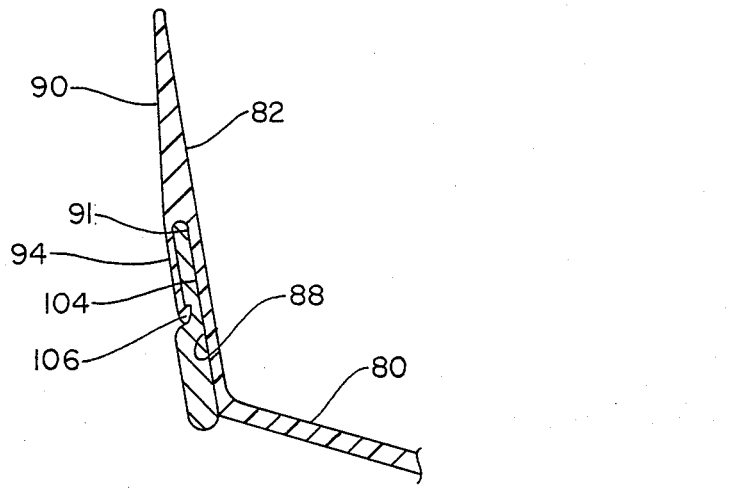

Referring now to FIGS. 5 and 6 as well as FIGS. 3 and 4, the crown 82 of visor 78 has a recess 88 opening onto the inner, or user adjacent side 90 of that visor component. The perspiration absorbing component 22 of sweatband 20 (shown diagrammatically in FIGS. 5 and 6) is seated in and against the bottom wall 91 of recess 88 and is positioned relative to visor 78 in a vertical direction by the upper, end wall 92 of recess 88. As shown in FIG. 6, sweatband 20 and visor 78 are maintained in this assembled relationship by one or more (typically two, see FIG. 4) resiliently displaceable, crown-associated tabs 94 and by clips 96 and 98 at the rear ends 100 and 102 of visor sidepieces 84 and 86.

The visor crown-associated tabs 94 are integral, at the upper ends thereof, with the crown 82 of visor 78. They depend from crown 82 in generally parallel, spaced relationship to the bottom wall 91 of that recess 88 in crown 82 in which the perspiration absorbing component 22 of sweatband 20 is seated.

In assembling visor 78 to sweatband 20, the perspiration absorbing component 22 of the latter is displaced upwardly relative to the crown 82 of visor 78 into the gap or space 104 between crown 82 and each of the crown-associated tabs 94. Thereafter, the tab 94 tends to restore to a relaxed orientation relative to visor crown 82, clamping sweatband component 22 against the bottom 91 of recess 88 to maintain the illustrated, assembled relationship between sweatband 20 and visor 78.

To ensure that the visor 78 does not inadvertently separate from sweatband 20, integral, hooklike projections 106 may be provided at the lower, free ends of tabs 94. These will engage with the inner covering 28 of sweatband component 22 to keep the sweatband and visor 78 from coming apart.

Referring again to FIG. 4, I pointed out above that the visor 78 of article 76 is also secured to the sweatband 20 of that article by clips 96 and 98 at the rear ends 100 and 102 of visor sidepieces 84 and 86. Clips 96 and 98 will be similar, if not identical. Consequently, only clip 96 will be disclosed herein.

That component has cooperating, upper and lower, resiliently displaceable tabs 108 and 110 which are integral with the sidepiece 84 of visor 78 at their upper and lower ends and spaced from the sidepiece to provide a sweatband receiving space (not shown) therebetween. There is a gap 112 between the lower end of tab 108 (which depends from the upper edge 114 of sidepiece 84) and lower tab 110 (which extends upwardly from the lower edge 116 of that sidepiece). Tabs 108 and 110 can be sprung apart and/or sweatband component 24 compressed to introduce the sweatband into the space between sidepiece 84 and clip members 108 and 110 through this gap. Thereafter, these members or tabs 108 and 110 tend to relax toward sidepiece 84, securely retaining the sidepiece to the sweatband.

Tabs 108 and 110 may of course be replaced with devices of a different nature but having the same function—for example, strips of a flexible material faced with an adhesive for bonding one tab to a cooperating one after the visor and sweatband are assembled or for bonding the tab directly to the sweat band.

It will of course be appreciated by those to whom this specification is addressed that the components of visor 78 may be designed in a manner differing considerably from those of the representative visor shown in FIGS. 3 and 4, either for aesthetic reasons or to provide the wanted shield. Depending upon the particular configuration that is employed, the rearwardly extending sidepieces 84 and 86 of the visor may be extensions of bill 80 rather than crown 82. Also, again dependent upon the configuration of the visor, the resilient tabs or clamps 108 and 110 at the free (rear) ends 100 and 102 of sidepieces 84 and 86 may secure those sidepieces to the moisture absorbing component 22 of sweatband 20 rather than to the elastically extensible component 24 of the sweatband.

From the foregoing, it will be apparent to the reader that my invention may be embodied in many specific forms not specifically disclosed above without departing from the spirit or essential characteristics of the invention. The embodiments of the invention disclosed herein are therefore to be considered in all respects as illustrative and not restrictive. The scope of the invention is instead indicated by the appended claims, and all changes which come within the meaning and range of the equivalency of the claims are therefore intended to be embraced therein.

What is claimed is:

1. A sweatband which has: a first component for absorbing perspiration from the skin of a user and a second, separate component for holding said first component against that part of the user's skin from which perspiration is to be absorbed, said first component being essentially inextensible and having an elongated core fabricated from a porous, predominantly open cell, moisture absorbent, synthetic polymer; a permeable covering overlying the inner side of said core and adapted to be in contact with the user's skin, said covering being fabricated from a chamois material which is soft and pliable and capable of promoting the transfer of moistur from the user's skin to the core of said first component; and a second, permeable covering overlying the outer side of said core, said second covering being made from a porous fabric which is capable of promoting the evaporation of moisture from said core into the ambient surroundings; the second component for holding the first component against the user's skin comprising an elongated, elastically extensible member; one end of said second, elastically extensible member being fixed to one end of said first component; and the other end of said elastically extensible member being fixed to the other end of said first component.

2. An article of apparel for absorbing perspiration from a wearer's forehead and for shielding the wearer's eyes, said article of apparel comprising: a sweatband and a visor assembled to said sweatband, said sweatband including a first, elongated, perspiration absorbing component and a second, also elongated component for holding the moisture absorbing component against the wearer's forehead, said visor having: a crown juxtaposed to the first sweatband component on the outer side thereof; a bill adapted to shade the wearer's eyes; and means for affixing said visor to said sweatband, the crown of said visor being recessed to accommodate said first, perspiration absorbing component of said sweatband.

3. An article of manufacture as defined in claim 2 wherein the crown of said visor has at least one elastically displaceable tab which is engageable with the inner side of the first, perspiration absorbing component of the sweatband to clamp said sweatband component in the recess in said visor and thereby secure said visor to said sweatband.

4. An article of apparel as defined in claim 3 wherein the elastically displaceable tab has a free end and wherein there is a hooklike projection at said free end that is engageable with the first, perpiration absorbing component of the sweatband to provide a secure, positive connection between said visor and said sweatband.

5. An article of apparel as defined in claim 4 wherein the visor has sidepieces at the opposite sides thereof and extending rearwardly relative to said bill and said crown when the article is worn and wherein the means for securing said visor to said sweatband comprises means at the rear end of each said sidepiece for clamping said sidepiece to one of the components of the sweatband.

6. An article of manufacture as defined in claim 5 wherein the means for clamping each said sidepiece of said visor to said sweatband comprises cooperating, elastically displaceable, upwardly and downwardly extending tabs, there being a gap between the apposite ends of the tabs and the latter being spaced from the sidepiece, whereby said tabs can first be sprung away from said sidepiece to enlarge said gap and allow said sweatband to be displaced through said gap into the space between said tabs and said sidepiece and then released to resiliently clamp said sweatband against said sidepiece.

7. An article of apparel for absorbing perspiration from a wearer's forehead and for shielding the wearer's eyes, said article of apparel comprising: a sweatband and a visor assembled to said sweatband, said sweatband including: a first, elongated, moisture absorbing component and a second, also elongated component for holding the moisture absorbing component against the wearer's forehead, said visor having: a crown portion, a bill portion, and sidepieces, said crown portion being juxtaposable to the first sweatband component on the outer side thereof, said bill portion being adapted to shade the wearer's eyes, said sidepieces being located at the opposite sides and extending rearwardly relative to said bill and crown portions when the article is worn, and said article of apparel also having means for securing said visor to said sweatband, said securing means comprising means with components at the rear end of each said sidepiece and surrounding said sweatband for clamping said sidepiece to the sweatband.

8. A article of apparel as defined in claim 7 wherein said first sweatband component is essentially inextensible and has: an elongated core fabricated from a porous, predominantly open cell, moisture absorbent, synthetic polymer; a permeable covering overlying the inner side of said core and adapted to be in contact with the wearer's forehead, said covering being fabricated from a chamois material which is soft and pliable and capable of promoting the transfer of moisture from the wearer's forehead to the core of said first component; and a second, permeable covering overlying the outer side of said core, said second covering being made from a fabric which is capable of promoting the evaporation of moisture from said core into the ambient surroundings, the second sweatband component comprising an elongated, elastically extensible member; one end of said second, elastically extensible member being fixed to one end of said first component; and the other end of said elastically extensible member being fixed to the other end of said first component.

9. An article of apparel as defined in claim 7 wherein the crown portion of said visor is recessed to accommodate said first, perspiration absorbing component of said sweatband.

10. An article of manufacture as defined in claim 9 wherein the crown portion of said visor has at least one elastically displaceable tab which is engageable with the inner side of the first, perspiration absorbing component of the sweatband to clamp said sweatband component in the recess in said visor and thereby secure said visor to said sweatband.

11. An article of apparel as defined in claim 10 wherein the elastically displaceable tab has a free end and wherein there is a hooklike projection at said free end that is engageable with the first, perspiration absorbing component of the sweatband to provide a secure, positive connection between said visor and said sweatband.

12. An article of manufacture as defined in claim 7 wherein the means for clamping each said sidepiece of said visor to said sweatband comprises cooperating, elastically displaceable, upwardly and downwardly extending tabs, there being a gap between the apposite ends of the tabs and the latter being spaced from the sidepiece, whereby said tabs can first be sprung away from said sidepiece to enlarge said gap and allow said sweatband to be displaced through said gap into the space between said tabs and said sidepiece and then released to resiliently clamp said sweatband against said sidepiece.

13. An article of apparel for absorbing perspiration from the forehead of and shielding a wearer's eyes, said article of apparel comprising: a sweatband and a visor assembled to said sweatband, said sweatband including: a first, elongated, perspiration absorbing component and a second, also elongated component for holding the moisture absorbing component against a wearer's forehead; said visor having a crown juxtaposed to the first sweatband component on the outer side thereof, a bill adapted to shade the wearer's eyes, sidepieces at the opposite sides of and extending rearwardly relative to said bill and said crown when the article is worn, and means for securing said visor to said sweatband, said securing means comprising means at the rear end of each said sidepiece for clamping the sidepiece to one of the components of the sweatband; the clamping means each including cooperating, elastically displaceable, upwardly and downwardly extending tabs; there being a gap between the apposite ends of the tabs; and the latter being spaced from the sidepiece, whereby said tabs can first be sprung away from said sidepiece to enlarge said gap and allow said sweatband to be displaced through said gap into the space between said tabs and said sidepiece and then released to resiliently clamp said sweatband against said sidepiece.

14. An article of apparel as defined in claim 13 wherein said first sweatband component is essentially inextensible and has: an elongated core fabricated from a porous, predominantly open cell, moisture absorbent, synthetic polymer; a permeable covering overlying the inner side of said core and adapted to be in contact with the wearer's forehead, said covering being fabricated from a chamois material which is soft and pliable and capable of promoting the transfer of moisture from the wearer's forehead to the core of said first component; and a second, permeable covering overlying the outer side of said core, said second covering being made from a fabric which is capable of promoting the evaporation of moisture from said core into the ambient surroundings; the second sweatband component comprising an elongated, elastically extensible member; one of said second, elastically extensible member being fixed to one end of said first component; and the other end of said elastically extensible member being fixed to the other end of said first component.

15. An article of apparel as defined in claim 13 wherein the crown of said visor is recessed to accommodate said first, perspiration absorbing component of said sweatband.

16. An article of manufacture as defined in claim 15 wherein the crown of said visor has at least one elastically displaceable tab which is engageable with the inner side of the first, perspiration absorbing component of the sweatband to clamp said sweatband component in the recess of said visor and thereby secure said visor to said sweatband.

17. An article of apparel as defined in claim 16 wherein the elastically displaceable tab has a free end and wherein there is a hooklike projection at said free end that is engageable with the first, perspiration absorbing component of the sweatband to provide a secure, positive connection between said visor and said sweatband.

* * * * *

UNITED STATES PATENT AND TRADEMARK OFFICE
CERTIFICATE OF CORRECTION

PATENT NO. : 4,856,116

DATED : August 15, 1989

INVENTOR(S) : Lloyd S. Sullivan

It is certified that error appears in the above-identified patent and that said Letters Patent is hereby corrected as shown below:

Column 2, line 43, after the word "have" insert a --comma--.

Column 2, line 61, "Romera" should read --Romero--.

Column 3, line 11, after the word "ball" insert a --period--.

Column 3, line 64, "modes" should read --modest--.

Column 4, line 39, "of" should read --or--. (2nd Occurrence)

Column 4, line 67, omit the word "to".

Column 5, line 29, "components" should read --component--.

Column 6, line 38, "identified" should read --identical--.

UNITED STATES PATENT AND TRADEMARK OFFICE
CERTIFICATE OF CORRECTION

PATENT NO. : 4,856,116

DATED : August 15, 1989

INVENTOR(S) : Lloyd S. Sullivan

It is certified that error appears in the above-identified patent and that said Letters Patent is hereby corrected as shown below:

IN THE CLAIMS:

Column 8, line 20, "moistur" should read --moisture--.

Column 8, line 56, "perpiration" should read --perspiration--.

Signed and Sealed this

Sixteenth Day of July, 1991

*Attest:*

HARRY F. MANBECK, JR.

*Attesting Officer*     *Commissioner of Patents and Trademarks*